United States Patent
Berlinger et al.

(10) Patent No.: US 10,391,334 B2
(45) Date of Patent: *Aug. 27, 2019

(54) CBCT AND X-RAY COMBINED SETUP WITH X-RAY VERIFICATION OF PATIENT POSITIONING

(71) Applicant: Brainlab AG, Munich (DE)

(72) Inventors: Kajetan Berlinger, Munich (DE); Sebastian Knorr, Munich (DE); Cornel Schlossbauer, Alling (DE); Joerg Rehs, Munich (DE)

(73) Assignee: Brainlab AG, Munich (DE)

( * ) Notice: Subject to any disclaimer, the term of this patent is extended or adjusted under 35 U.S.C. 154(b) by 103 days.

This patent is subject to a terminal disclaimer.

(21) Appl. No.: 15/818,243

(22) Filed: Nov. 20, 2017

(65) Prior Publication Data

US 2018/0071551 A1 Mar. 15, 2018

Related U.S. Application Data

(63) Continuation of application No. 14/759,905, filed as application No. PCT/EP2013/050240 on Jan. 9, 2013, now Pat. No. 9,849,308.

(51) Int. Cl.
*A61N 5/10* (2006.01)
*G06T 7/30* (2017.01)
(Continued)

(52) U.S. Cl.
CPC ........... *A61N 5/1049* (2013.01); *A61B 6/032* (2013.01); *A61B 6/04* (2013.01); *A61B 6/4085* (2013.01);
(Continued)

(58) Field of Classification Search
CPC .............................. A61N 5/10–5/1084; A61N 2005/1085–2005/1098;
(Continued)

(56) References Cited

FOREIGN PATENT DOCUMENTS

WO 2012095172 7/2012

OTHER PUBLICATIONS

European Patent Office, International Search Report of PCT/EP2013/050240 dated May 2, 2013, pp. 1-4, European Patent Office, Rijswijk, Netherlands.
(Continued)

*Primary Examiner* — Thaddeus B Cox
(74) *Attorney, Agent, or Firm* — Middleton Reutlinger (57) ABSTRACT

The disclosure is directed to a radiotherapy system having a treatment device for treating a treatment body part of a patient with a treatment beam arrangement. The treatment device is included with a couch for placing the patient and includes a medical imaging devices for outputting three-dimensional cone-beam computed tomography images to a computer, and a medical imaging x-ray device for generating at least one x-ray image, if the patient is placed on the couch for treatment, and for outputting at least one x-ray image to the computer. The system will output movement control data to control the relative position of the treatment body part relative to the treatment beam if it is determined there is the offset between the position of the treatment body part relative to the bony structure as described by the image data and the position of the treatment body part relative to a bony structure.

14 Claims, 2 Drawing Sheets

(51) Int. Cl.
  *A61B 6/04* (2006.01)
  *A61B 6/03* (2006.01)
  *A61B 6/00* (2006.01)
  *G06T 7/00* (2017.01)

(52) U.S. Cl.
  CPC ........... *A61N 5/107* (2013.01); *A61N 5/1037* (2013.01); *A61N 5/1071* (2013.01); *A61N 5/1077* (2013.01); *G06T 7/0012* (2013.01); *G06T 7/30* (2017.01); *A61N 2005/1061* (2013.01); *A61N 2005/1062* (2013.01); *A61N 2005/1072* (2013.01); *A61N 2005/1074* (2013.01); *G06T 2207/10072* (2013.01)

(58) Field of Classification Search
  CPC .................................. G06T 7/30–7/38; G06T 2207/10072–2207/10084; G06T 2207/10116–2207/10124
  See application file for complete search history.

(56) References Cited

OTHER PUBLICATIONS

Chang, Zheng, et al, "6D image guidance for spinal non-invasive stereotactic body radiation therapy: Comparison between ExacTrac X-ray 6D with kilo-voltage cone-beam CT", Radiotherapy and Oncology: Journal of the European Society for Therapeutic Radiology and Oncology, Apr. 2010, vol. 95, No. 1, Apr. 2010, pp. 116-121.

Steininger P, et al., "Paper; Auto-masked 2D/3D image registration and its validation with clinical cone-beam computed tomography; Auto-masked 2D/3D image registration and its validation with clinical cone-beam computed tomography", Physics in Medicine and Biology, Institute of Physics Publishing, Bristol GB, vol. 57, No. 13, Jun. 15, 2012, pp. 4277-4292.

Wang, Z, et al., "Refinement of Treatment Setup and Target Locablization Accuracy Using Three-Dimensional Cone-Beam Computed Tomography for Stereotactic Body Radiotherapy", International Journal of Radiation: Oncology Biology Physics, Pergamon Press, USA, vol. 73, No. 2, Feb. 2009, pp. 571-577.

Markelj, P, et al., "A review of 3D/2D registration methods for image-guided interventions.", Medical Image Analysis Apr. 2012, vol. 16, No. 3, Apr. 2012, pp. 642-661.

CBCT AND X-RAY COMBINED SETUP WITH X-RAY VERIFICATION OF PATIENT POSITIONING

The present invention is directed to a method, in particular a data processing method, for determining the consistency of registration of the position of a treatment body part to be treated by radiotherapy in accordance with claim 1, a corresponding program and computer running that program as well as a radiotherapy system comprising that computer. Furthermore, the invention is directed to a method for controlling that radiotherapy system.

When planning a radiotherapy procedure for a specific patient, it is desirable to have information about the position of in particular soft tissue relative to the position of a beam of ionizing radiation which is used to conduct the treatment. This is because the treatment targets such as tumours are frequently located in soft tissue. However, it is comparably difficult to visualize soft tissue with easily applicable medical imaging methods such as conventional x-ray. Known approaches involve taking a computed tomography of the patient's body prior to placing him in position for treatment. It is then assumed that the spatial relationship between soft tissue and bony structures which may both be visualized in a CT image remains constant irrespective of the patient's position or state of motion. When the patient has been placed in position for radiotherapy, for example on a couch of a radiotherapy system, x-ray images are then taken of the patient's body and the position of the bony structure is compared with a position of the treatment beam. Based on the information about the spatial relationship between the soft tissue and the bony structures, the spatial relationship between the soft tissue and the treatment beam can thus be established. Thereby, a shift in the position of the soft tissue relative to the position of the treatment beam can be determined and the patient can be moved correspondingly such that the patient is correctly positioned relative to the treatment beams such that the desired soft tissue can be irradiated with treatment radiation.

However, such an approach can lead to a positional offset of the soft tissue from the desired position as the precise spatial relationship between the bony structures visualized by x-ray imaging and the soft tissue may not be known. In particular, the soft tissue may—for example due to its elastic properties—have changed its spatial properties (in particular, size and/or shape) such that it is no longer covered by the treatment beam in the desired manner. To this end, an approach has been proposed which involves generating digitally reconstructed radiographs (DRRs) from CBCT (cone beam computed tomography) images of the patient's body after positioning the patient in place for radiotherapy. The CBCT images are then subjected to an image fusion algorithm in order to fuse them into the predetermined CT images, while a new x-ray image is acquired. That approach allows for comparison of the CBCT and the x-ray images and thereby determining the soft-tissue-shift. However, any shift in the fusion that resulted from the soft tissue-based registration of the CT and CBCT images can no longer be extracted in such an approach once the fusion has been effected. Errors leading to such a shift in the fusion may be due to for example a bad user-conducted fusion, a bad calibration of the CBCT system or a data import error.

A problem to be solved by the invention therefore is to provide an improved method of determining whether a patient is correctly positioned for radiotherapy.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The present invention in particular provides a method, more particularly a data processing method, for determining the consistency of registration of the positional treatment body part to be treated by radiotherapy with a treatment beam arrangement over at least one position of a treatment beam which is issued by a treatment device. It is preferably determined whether the registration of the position of the treatment body part is consistent with the treatment beam arrangement which comprises at least one treatment beam, in particular at least one position of a treatment beam. The treatment body part is in particular a soft tissue part of an anatomical structure of a patient's body. Such a soft tissue part may be for example a part of the brain, lung or liver of the patient. The treatment device preferably is any known device which is used for application of treatment radiation to a patient's body such as for example a particle accelerator, x-ray tube or radioactive emitter. Treatment radiation in the context of this disclosure is understood to be any type of in particular ionizing radiation which is used in radiotherapy. Such treatment radiation is advantageously applied in a beam, i.e. a flux of particles which have an ionizing energy, the flux being at least partly continuous. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathologic structure or tissue such as a tumour are treated using ionising radiation. The tumour is then an example of a treatment body part. The inventive method preferably comprises the following steps and is advantageously constituted to be executed by a computer.

Preferably, CT data comprising predetermined CT information about a predetermined position of the treatment body part relative to a bony structure of the patient's body is acquired. In the context of this disclosure, the abbreviation CT is understood to denote "computed tomography", i.e. a three-dimensional, x-ray-based medical imaging method. The CT data is preferably generated before treatment of the patient in particular by radiotherapy commences and merely acquired by the inventive method in the sense that it is read by a computer on which the inventive method is executed. The term of bony structure in the context of this invention encompasses any part of the patient's skeleton, in particular a bone in the strict sense or cartilage. The position of the treatment body part relative to the bony structure is described in particular by its distance, direction and preferably also orientation relative to the bony structure. It is assumed that the position of the treatment body part relative to the bony structure is generally constant and in particular remains the same throughout execution of the inventive method. On that basis, information about the position of the treatment body part (which in particular comprises or consists of soft tissue such as lung tissue, brain tissue or stomach tissue) can be determined based on information about the position of the bony structure. Within the framework of this disclosure, positions can be described in a coordinate system in which the patient rests (in particular, a patient-centered coordinate system which has its origin inside or on the surface of the patient's body) or a global coordinate system which is for example centered in a room in which the treatment device is located.

Furthermore, the CT information also comprises information about (i.e. describing) a first position (in particular a predetermined first position) of the bony structure relative to the treatment beam arrangement. In the following, a short definition of the term "treatment beam arrangement" is offered.

A treatment body part can be treated by one or more treatment beams issued from one or more directions at one or more times. Thus the treatment by means of the at least one treatment beam follows a spatial pattern and a time pattern. To cover the spatial and time features of the treatment by means of the at least one treatment beam, the term "beam arrangement" is used. The beam arrangement is an arrangement of at least one treatment beam.

The beam positions describe the positions of the treatment beams of the beam arrangement. The arrangement of beam positions is called positional arrangement. A beam position is preferably defined by the beam direction and additional information which allows to assign a specific location in particular a three-dimensional space to the treatment beam, for example information about the coordinates in a defined coordinate system. The specific location is one point on preferably a straight line. This line is called "beam line" and runs in the beam direction and for instance runs along the central axis of the treatment beam. The defined coordinate system is preferably defined relative to the treatment device or relative to at least part of the patient's body. The positional arrangement comprises (in particular consists of) at least one beam position, in particular a discrete set of beam positions (e.g. two or more different beam positions) or a continuous multiplicity (manifold) of beam positions.

During treatment, at least one (i.e. one or more) treatment beam adopts in particular the treatment beam positions defined by the positional arrangement simultaneously or sequentially (the latter in particular in case there is just one beam source to emit a treatment beam). If there are several beam sources, at least a sub-set of all beam positions can also be adopted simultaneously by treatment beams during the treatment. In particular one or more sub-sets of the treatment beams can adopt the beam positions of the arrangement in accordance with a pre-defined sequence. A sub set of treatment beams comprises one or more treatment beams. The full set of treatment beams which comprise one or more treatment beams and which adopts all beam positions defined by the positional arrangement is the beam arrangement.

Based on the CT information about the position of the treatment body part relative to the bony structure and about the first position of the bony structure relative to the treatment beam arrangement, a general transformation (in particular function) for determining the position of the treatment body part relative to the treatment beam arrangement based on such CT information can be determined.

Preferably, x-ray data comprising x-ray information about an second position (in particular an actual second position) of the bony structure relative to the treatment beam arrangement is acquired. The x-ray data is generated preferably after placing the patient in position ready for radiotherapy and is in particular generated by applying a conventional x-ray method to the patient's body. The x-ray method is executed in particular by activating in particular two conventional x-ray tubes which are located symmetrical relative to a longitudinal central plane of symmetry of a bed (which may also be called a couch) on which the patient is placed for radiotherapy. A detection of the x-ray transmission signals is preferably conducted by digital x-ray sensors which are located for example in the floor to the longitudinal sides of the couch. Preferably, the spatial relationship (in particular, the position and/or orientation) of the x-ray emitters relative to the x-ray sensor is known, in particular predetermined, and advantageously fixed.

Based on the x-ray data and the CT data, preferably bony structure position first transformation data is determined. The bony structure position first transformation data comprises in particular bony structure position first transformation information about a first transformation between the first position and the second position of the bony structure. This difference in position is also called bony-anatomy-shift. In the context of this disclosure, a transformation is understood to be in particular a coordinate transformation, more particularly a linear transformation which can be embodied by a matrix. Where applicable, the transformation may be said to comprise or be a mapping and can also be embodied by a single-column matrix, i.e. a vector. The first transformation describes in particular the mapping between the first position and the second position of the bony structure. Based on the assumption of a constant position of the treatment body part relative to the bony structure, the position of the treatment body part relative to the treatment beam arrangement may in the framework of the invention therefore also be determined based on the x-ray data. In particular, the position of the treatment body part relative to the treatment beam arrangement after placing the patient's body ready for radiotherapy may be determined based on the x-ray data.

Preferably, CBCT data is acquired which comprises CBCT information about the position of the treatment body part relative to the treatment beam arrangement. In the context of this disclosure, the abbreviation CBCT is understood to mean "cone-beam computed tomography". The CBCT data is preferably acquired by using a CBCT device on the patient. The CBCT device is preferably included in a radiotherapy system used for conducting the envisaged radiotherapy treatment and therefore has a known, in particular predetermined spatial relationship (in particular, position) relative to the treatment beam arrangement. Thereby, the position of imaged entities (such as the treatment body part relative) to the treatment beam arrangement can be determined. Alternatively or additionally, the CBCT information comprises or consists of information about the position of the treatment body part relative to the bony structure.

Preferably, bony structure position second transformation data which comprises bony structure position second transformation information is determined based on the CBCT data (in particular, the CBCT information) and the CT data (in particular, the CT information). The bony structure position second transformation is in particular information about a second transformation between the first position and a third position of the bony structure relative to the treatment beam arrangement. The third position is in particular a position (more particularly, an actual position) of the bony structure after the bony structure has been moved to cancel an offset between the position of the bony structure and the position of the treatment beam arrangement as described by the first transformation. Such a movement is also termed "primary correction of the patient's (second) position". The second transformation therefore describes any offset of the bony structure from a position to which it was moved during a primary correction of the position of the patient's body on the basis of the x-ray data. This procedure provides the additional advantage of being able to determine an offset between two different image fusion modalities, namely firstly the image fusion of the CT data and the x-ray data and, secondly, the image fusion of the CBCT data and the CT data. This offset can be determined in particular on the basis of the determined position of the bony structure.

The bony structure position first transformation data (in particular the bony structure position first transformation information) and the bony structure position second transformation data (in particular the bony structure position second transformation) then preferably serve as a basis for determining transformation difference data. The transformation difference data comprises in particular transformation difference information about the difference between the first and second transformations. Further, it is preferably determined whether the transformation difference information indicates that there in fact is a difference between the first and second transformation. If it does indicate that there is a difference, the bony structure is preferably moved relative to the treatment beam arrangement so that the difference between the first and second transformation is compensated. Thereby, an offset in tracking soft tissue movement based on the x-ray data and based on the CBCT data can be eliminated. The difference between the first and second transformations can be described in particular by a matrix or vector, respectively, and/or a scalar value determined by subtracting and/or dividing the first and second transformations from or by each other, respectively.

The transformation difference information can in particular serve as a basis for controlling the position of the treatment body part relative to the treatment beam arrangement during radiotherapy. In view of the above-described method, this allows for tracking patient movements during application of treatment radiation on the basis of CBCT data which allows to avoid taking further CT data and applying the associated radiation dose to the patient. Compared to the above-described conventional approaches, the present invention provides the advantage of employing two different image fusion modalities, namely image fusion between CT data and x-ray data, and image fusion between CBCT data and CT data. In particular, the bony structure position first transformation data is determined based on an applying an elastic fusion algorithm to the CT data and the x-ray data and the bony structure position second transformation data is determined based on an applying an elastic fusion algorithm to the CBCT data and the CT data. These two image fusion procedures are completely decoupled from one another and, whereby the problem of potentially unrecoverable setup errors due to fusing CT information and CBCT information during primary positioning (in particular, as a basis for primary correction of the patient's position) of the patient can be avoided. Furthermore, a plausibility check (consistency check) for the respectively determined position of the bony structure relative to the treatment beam arrangement can be provided, i.e. a second transformation can be used as a measure for correctness of the first transformation, wherein small deviations between the first and second transformation are to be expected and tolerated in the range of typical soft tissue movements (which may be due to for example vital movements, i.e. movements due to heart beat, breathing or bowel movements).

Preferably, the first transformation is determined based on the CT information about the first position of the bony structure relative to the treatment beam arrangement. The second transformation is preferably determined based on the CT information about the position of the treatment body part relative to the bony structure. To this end, it is in particular assumed that the position of the treatment body part relative to the bony structure at the point of time at which the CBCT data is acquired is identical to the position of the treatment body part relative to the bony structure described by the CT information.

Preferably, the inventive method comprises a step of determining whether the first transformation is equal to identity. If it is determined that the first transformation is not equal to identity, the bony structure is then preferably moved relative to the treatment beam arrangement so that the first transformation becomes identity. This movement preferably is part of (in particular constitutes) the primary correction of the patient's position. In particular, the bony structure is moved in a direction described by the first transformation and/or its inverse, depending on the definition of mapping directions. By doing so, the treatment body part is in particular positioned at a position corresponding to its first position relative to the treatment beam arrangement so that the treatment body part is at a location which has been planned for conducting radiotherapy. This supports having the treatment body part at a position suitable for irradiation by treatment radiation. In particular, the so-called bony anatomy shift between the position of a bony structure in the CT data and in the x-ray data can be eliminated in this manner.

Preferably, the bony structure position second transformation data is determined by determining at least one two-dimensional digitally reconstructed radiograph (DRR) from a three-dimensional CBCT image described by the CBCT information. The digitally reconstructed radiograph in particular matches at least one x-ray image described by the x-ray information, the matching resulting in particular from a simulation of at least one imaging geometry given for generating at least one two-dimensional digitally reconstructed radiograph (DRR). The imaging geometry is preferably known to the inventive method (in particular, it is predetermined) and can be described e.g. the position of the x-ray tube used for generating at least one x-ray image relative to the patient's body and the position of the x-ray detector relative to the patient's body and/or the x-ray tube. Advantageously, the imaging geometry is also described by the emission characteristics of the x-ray tube, e.g. the opening angle of the x-ray beam cone. If a "DRR" matches an x-ray image, the simulated imaging geometry (used to generate the DRR) is called matching imaging geometry. To each of the at least one two-dimensional x-ray image corresponds a respective matching imaging geometry. The matching of a DRR with an x-ray image is preferably performed based on (in particular only based on or predominantly based on) the bony structure such that the bony structure shown in the DRR and shown in the x-ray image match with each other, in particular achieve a best match. In particular, other parts of the anatomical structure which are not part of the bony structure are weighed less in the matching process than the bony structure. In particular, a segmented bony structure is used for matching, in particular only the bony structure is used for matching. Preferably, there are at least two x-ray images which are respectively to be matched with one of the simulated DRRs. Preferably, a plurality of DRRs are generated and the matching DRRs are selected out of the plurality of DRRs.

For moving the patient, in particular at least one of the bony structure and the treatment body part, relative to the treatment beam arrangement, preferably patient movement control data is determined by a computer of the radiotherapy system used for conducting the envisaged radiotherapy treatment. The patient movement control data is preferably determined based on the bony structure position first transformation information and, if applicable, independently based on the bony structure position second transformation information and comprises patient movement control information which describes (in particular represents) commands which are to be sent to and executed by e.g. a moving mechanism of a couch of the radiotherapy system on which the patient is placed for treatment. The couch (with the patient placed on it) is then moved by the moving mechanism in a direction described by the patient movement control information.

Preferably, the CT data, the x-ray data and the CBCT data are generated at each a different point in time. In particular, the CT data is generated at a point of time called pre-alignment time, i.e. before the patient is placed in position for radiotherapy. This position would be in particular a planned position, i.e. a position which is suitable for irradiating the planned treatment target which treatment radiation. Such positioning of the patient for radiotherapy is also called aligning the patient or alignment of the patient, respectively. The x-ray data is preferably generated after aligning the patient, and the CBCT data is preferably generated after the x-ray data. Further, preferably, the x-ray data is generated before moving the patient after primary alignment in order to correct any bony anatomy shift (i.e. before primary correction of the patient's position), and the CBCT data is generated after primary correction of the patient's position. In summary, the x-ray data is preferably generated before the CBCT data is generated and further preferably primary correction of the patient's body is conducted after the x-ray data has been generated and before the CBCT data is generated. To this end, preferably CBCT imaging control data is generated and also acquired by the inventive method. The CBCT imaging control data comprises in particular CBCT imaging control information which comprises instructions in particular for a computer to cause generation of the CBCT data (in particular, by a computer-controlled CBCT device) after a period of time during which the treatment body part has been treated by a treatment beam.

Alternatively or additionally, the CBCT data may be generated before treatment by radiotherapy commences. Bony structure position second data which is determined based on CBCT data which has been generated before radiotherapy commences is in particular used to determine an offset of the treatment body part from its position relative to the bony structure as described by the CT information. Such an offset is also termed soft-tissue-shift. It is then preferably determined whether the second transformation is equal to identity. If it is determined that the second transformation is not equal to identity, the bony structure and/or the treatment body part is then preferably moved relative to the treatment beam arrangement so that the second transformation becomes identity. For example, a couch on which the patient is placed for treatment is subjected to a corresponding movement. In general terms, one may say that the soft-tissue-shift is applied to the couch. In particular, the bony structure and/or the treatment body part is moved in a direction described by the second transformation and/or its inverse, depending on the definition of the mapping directions. An object of doing so is to move the treatment body part into its position relative to the treatment beam arrangement as it can be determined based on the CT data. In particular, the treatment body part is then moved into a planned position which was predetermined during planning of the envisaged radiotherapy treatment. This supports having the treatment body part at a position suitable for irradiation by treatment radiation.

The information about the bony-anatomy-shift serves in particular as basis for a calibration consistency check in which the calibration of positions which are considered for patient positioning is checked. The calibration consistency check in particular involves fusing the CBCT information with the CT information based on image features describing the bony structure. Based on the known information about the spatial relationship (in particular the position and preferably also the orientation) of anatomical structures described by the CT information and corresponding image features described by the x-ray information, the spatial relationship (in particular the position and preferably also the orientation) of the corresponding image features described by the CT information relative to the position of the treatment beam arrangement can be determined. In summary, the CBCT information is fused with the CT information, and the result of that fusion (a transformation, in particular the first transformation described by the bony structure position first transformation information) is compared to the result of fusing the x-ray information with the CT information (which is also a (a transformation, in particular the second transformation described by the bony structure position second transformation information) based on the position of image features describing the bony structure. From the result, the position of these image features in the CBCT information relative to the position of the treatment beam arrangement is then determined. Such a procedure is more accurate than relying on a known and in particular predetermined spatial relationship between the CBCT device and the position of the treatment beam arrangement, as first applying an x-ray correction leads to more accurate results in position determination.

In particular, the soft-tissue-shift can be eliminated in this manner. In particular, treatment of the treatment body part is interrupted before the CBCT data is generated and advantageously continued after the CBCT data has been generated. Therefore, the step of generating (and in particular also of acquiring) the CBCT data does not comprise or encompass any treatment of the human or animal body in particular by radiotherapy. By executing the instructions contained in the CBCT imaging control information to generate the CBCT data only after a (in particular) period of time, monitoring of a possible movement of the patient's body (in particular the treatment body part) during intervals of irradiation with treatment irradiation is supported. Thereby, the relative position between the treatment body part and the treatment device can be adjusted in order to support correct irradiation during a subsequent interval of irradiation.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The present invention is also directed to radiotherapy system which comprises the above-mentioned computer. Furthermore, the radiotherapy system comprises preferably the treatment device. Preferably, the treatment system comprises a couch for placing the patient thereon. The treatment device is preferably constituted to treat the treatment part if the patient is placed on the couch for treatment. In particular, the treatment device is constituted so that the relative positions between the beam positions relative to the treatment device are controllable (in particular settable) to that an arrangement of beam positions can be set, the relative positions of the set arrangement corresponding preferably to (in particular are identical with) with the relative positions between the beam positions of the planned arrangement. In particular the couch and the treatment device are constituted so that the relative position between the set arrangement of beam positions and the treatment body part is changeable.

Preferably the treatment system comprises a CBCT-device. The CBCT-device is constituted to generate the three-dimensional CBCT images. In particular, the computer comprises a database within which the relative position between the CBCT image generated by the CBCT-device and a reference system of the treatment device is known. Preferably, the relationship between a reference system within which the actual arrangement is set and the reference system of the CBCT image is stored in the data base and/or is determinable based on the data stored in the database of the computer and based on data describing the set actual arrangement.

According to an embodiment, the x-ray images are generated by means of the CBCT-device. According to another embodiment, an x-ray device (which is independent from the CBCT-device) is part of or associated with/attached to the radiotherapy system and is used for generating the two-dimensional x-ray images. Preferably, the database of the computer stores a positional relationship between the x-ray imaging geometry (or x-ray imaging geometries) and a reference system of the CBCT-image and/or a reference system within which the position of the actual arrangement is set. Preferably, after setting of the arrangement, the relative beam positions defined by the arrangement are fixed with respect to each other but, according to an embodiment, the position of set arrangement can be determined with respect to the treatment device. The actual arrangement is set in particular in accordance with control data (called arrangement control data which are provided (in particular received)). The arrangement control data can be set by an operator to comply as best as possible with the planned relative position under the assumption of an assumed position of the treatment body part (after placing the patient on the couch). The arrangement control data defines a position of the actual arrangement in the reference system of the arrangement.

According to an embodiment, the position of the couch is changeable by means of the alignment control data and/or x-ray based control data. Additionally or alternatively, the position of the actual arrangement within the reference system of the arrangement is changeable based on the alignment control data and % or the x-ray based position control data. Thus, the position of the treatment body part relative to the actual arrangement can be changed by changing the position of the couch and/or by changing the position of the actual arrangement within the reference system of the treatment device.

In particular, control signals are issued by the computer to the couch and/or to the treatment device for changing the relative position between the couch and the reference system of the treatment device.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The information on the imaging geometry preferably comprises information which allows the analysis image (x-ray image) to be calculated, given a known relative position between the imaging geometry analysis apparatus and the analysis object (anatomical body part) to be analysed by the x-ray radiation, if the object (anatomical body part) to be analysed is known, wherein "known" means that the spatial geometry (size and shape) of the analysis object is known. This means in particular that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The position and in particular orientation of the imaging geometry is in particular defined by the position of the x-ray device, in particular by the position of the x-ray source and the x-ray detector and/or in particular by the position of the multiplicity (manifold) of x-ray beams which pass through the analysis object and are detected by the x-ray detector. The imaging geometry in particular describes the position (in particular, the orientation) and the shape (for example, a conical shape exhibiting a specific angle of inclination) of said multiplicity (manifold). The position can in particular be represented by the position of an x-ray beam which passes through the centre of said multiplicity or by a position of a geometric object (such as a truncated cone) which represents the multiplicity (manifold) of x-ray beams. Information concerning the above-mentioned interaction is preferably three-dimensionally known, for example from a three-dimensional CT, and describes the interaction in a spatially resolved way for points and/or regions of the analysis object, in particular force all of the points and/or regions of the analysis object. Knowledge of the imaging geometry in particular allows a location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made in particular to the following publications:

"An Efficient and Accurate Camera Calibration Technique for 3D Machine Vision", Roger Y. Tsai. Proceedings of the IEEE Conference on Computer Vision and Pattern Recognition. Miami Beach. Fla., 1986, pages 364-374

"A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344. See also http://www.cs.cmu.edu/~rgw/TsaiDesc.html Publication by Ziv Yaniv, "Fluoroscopic X-ray Image Processing and Registration for Computer-Aided Orthopedic Surgery"

EP 08 156 293.6

U.S. 61/054,187

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information". Where in the context of this disclosure it is said that certain data or information forms a basis for determining other data or information, it is to be understood that this encompasses determining the other data or information from the certain data or information. Where in the context of this disclosure it is said that information is information about a specific entity, this encompasses the case of the information describing, in particular representing, that entity.

In this application, the term "image morphing" is also used as an alternative to the term "image fusion", but with the same meaning.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

In the following, specific embodiments of the invention are disclosed with reference to the figures which are to be understood as mere examples without limiting effect to the scope of the invention.

Figure 1:
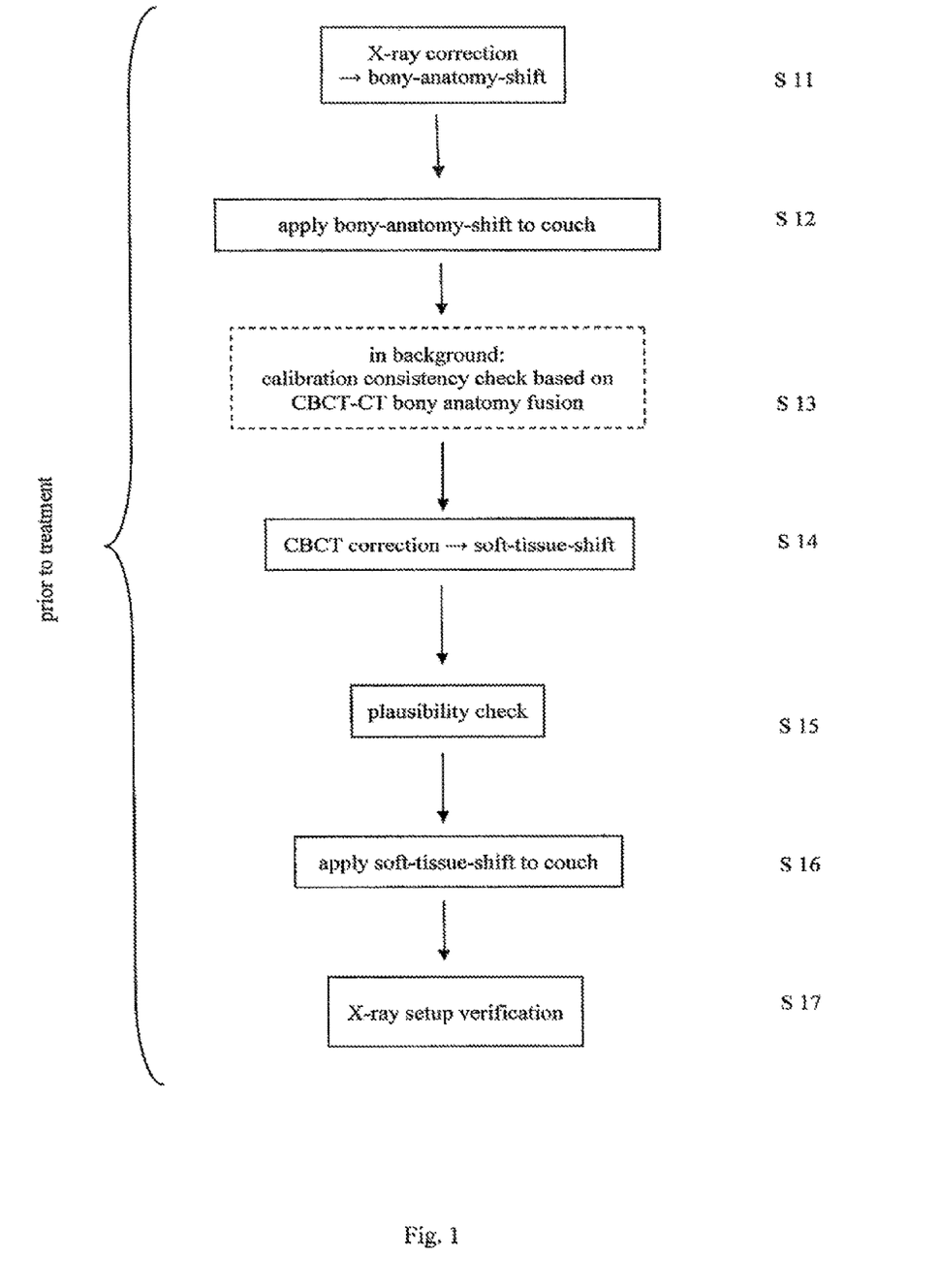
FIG. 1 shows an embodiment of the invention in which a plausibility check by comparison of bony-anatomy-shift and soft-tissue-shift is conducted prior to radiotherapy treatment.

FIG. 1 is a flow diagram of method steps to be executed for correction of both a bony-anatomy-shift and a soft-tissue-shift. In step S11, an x-ray correction is conducted by acquiring the x-ray data and determining the first transformation between the first position and the second position of the bony structure based on the x-ray data and predetermined CT data. The CT data is acquired in a method step preceding step S11 and is generated preferably outside of the method described by FIG. 1. The so determined transformation describes the bony-anatomy-shift which is then applied in step S12 to a couch of a radiotherapy system on which the patient is placed ready for radiotherapy treatment. In particular, the couch is moved in step S12 based on patient movement control data which has been determined by a computer of a radiotherapy system based on information about the bony-anatomy-shift (i.e. based on the bony structure position first transformation information) and has been sent to a moving mechanism which is operatively coupled to the couch in order to actuate the moving mechanism to move the couch based on the information about the bony-anatomy-shift.

Then, the CBCT data is generated and in step S13, the CBCT data is fused with the CT data based on image features describing the bony structure (i.e. bony anatomy of the patient's body). Based on the result of this fusion, a calibration consistency check with the CBCT information is conducted. This consistency check comprises determining whether the calibration of the anatomical structures of the patient's body described by the CBCT information, in particular of bony structures of the patient's body as described by the CBCT information, with the position of the treatment beam arrangement is correct. The calibration consistency check in particular is executed in the background which means that it is conducted without user interaction. Rather, import of the CBCT data and subsequent execution of the calibration consistency check is performed automatically.

Based on the so determined spatial relationship between structures represented by image features of the CBCT information and the treatment beam arrangement, the position of the treatment body part relative to the treatment beam arrangement is then determined in order to determine the soft-tissue-shift. Preferably, step S15 then continues with a plausibility check which determines whether the soft-tissue-shift is within predetermined limits. For example, typical ranges of soft-tissue-shift are considered to find out whether the determined soft-tissue-shift represents a plausible value. If this is the case, then step S16 continues with applying the soft-tissue-shift to the couch on which the patient has been placed in order to eliminate the soft-tissue-shift and to achieve the desired spatial relationship between the treatment body part and the treatment beam arrangement.

Application of the correct value of the soft-tissue-shift is then checked in step S17 by verification of the x-ray setup. In particular, an offset in the actual position of the bony structure relative to the treatment beam arrangement is expected which is equal to the negative value of the soft-tissue-shift. If it is determined that the offset equals this expected offset, the algorithm of FIG. 1 ends and the patient is considered to be correctly positioned for radiotherapy treatment. It is noted that radiotherapy treatment is executed only after execution of the method steps of FIG. 1, in particular the entirety of steps S11 to S17 is executed prior to treatment by radiotherapy.

Figure 2:
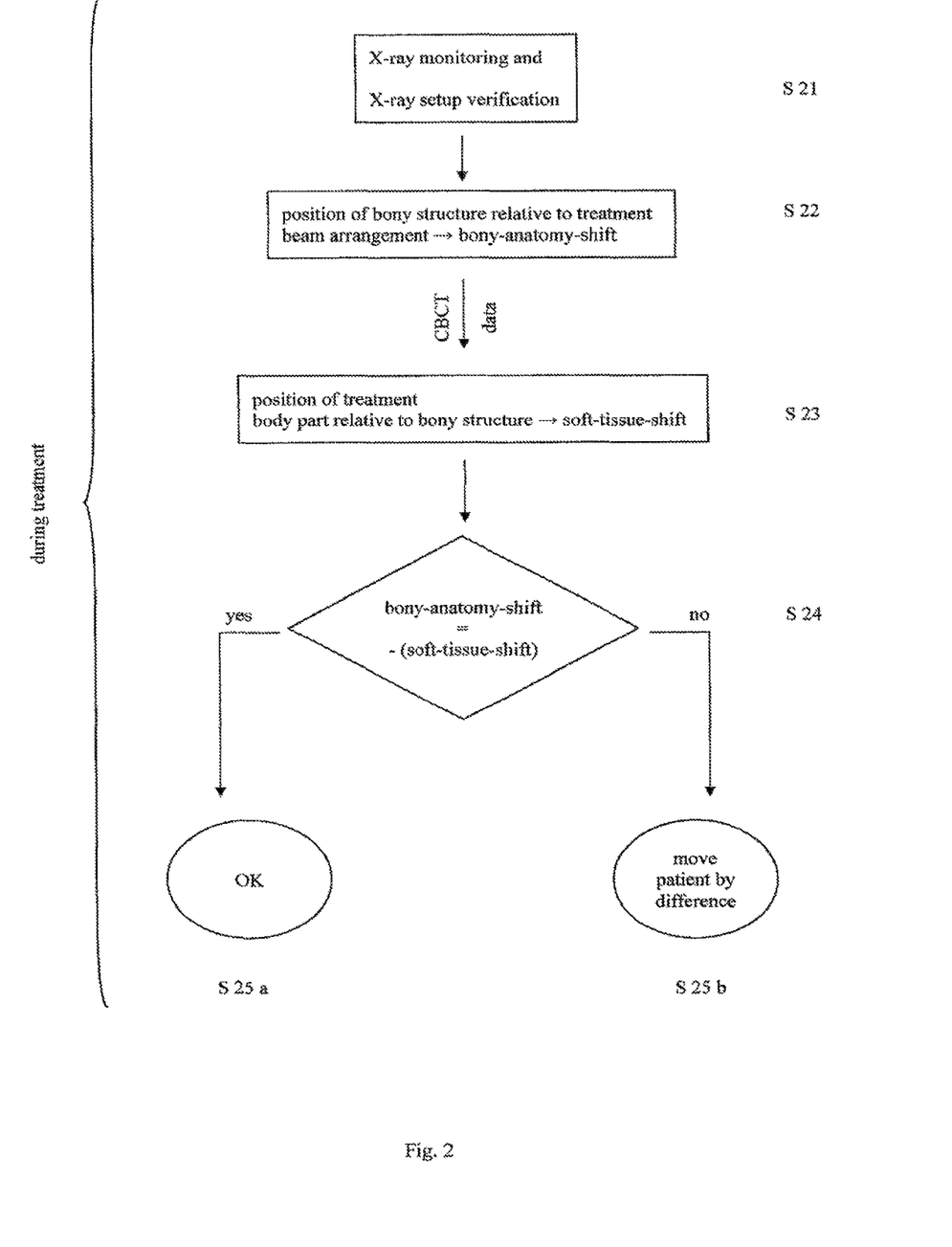
FIG. 2 shows a flow diagram comprising method steps for repeated verification of patient positioning in between treatment intervals.

FIG. 2 is a flow diagram comprising steps for continuing correct positioning of the patient during radiotherapy treatment. It is noted, however, that the entirety of method steps shown in FIG. 2 may be executed "during treatment" only in the sense that treatment itself, in particular irradiation with treatment radiation is interrupted for execution of the entirety of method steps shown in FIG. 2. Therefore, execution of the method steps shown in FIG. 2 does not comprise or encompass any step of treatment.

In step S21, again x-ray data is acquired after one (time) block of irradiating a patient with treatment radiation. Based on the thus acquired x-ray data, the afore mentioned x-ray setup verification of step S17 is repeated by determining in steps S22 and S23 the current bony-anatomy-shift and based on that bony-anatomy-shift and the CBCT data, the current soft-tissue-shift. It is then evaluated in step S24, whether the bony-anatomy-shift equals the negative value of the soft-tissue-shift, i.e. whether the two shifts cancel each other out. If step S24 determines that the bony-anatomy shift and the soft-tissue-shift add to zero, i.e. cancel each other out, the method of FIG. 2 finishes in step S25a with the result that positioning of the patient is as desired. If it is determined, that the two shifts do not add to zero, i.e. do not cancel each other out, the method of FIG. 2 continues to step S25b in which the patient is moved by the difference between the two shifts, in particular based on patient movement control data comprising patient control movement information for driven movement of the couch.

The invention claimed is:

1. A radiotherapy system, comprising:
a treatment device for treating a treatment body part of a patient with a treatment beam arrangement;
a couch for placing the patient, the treatment device constituted for treating the treatment body part, if the patient is placed on the couch for treatment;
a first medical imaging device constituted for generating a three-dimensional first image and for generating at least one second image, if the patient is placed on the couch for treatment and for outputting the three-dimensional first image and the at least one second image to a computer; or
a second medical imaging device constituted for generating a three-dimensional first image and for outputting the three-dimensional first image to a computer, and a third medical imaging device for generating at least one second image, if the patient is placed on the couch for treatment, and for outputting the at least one second image to the computer;
wherein the radiotherapy system further comprises the computer, wherein the computer comprises at least one processor which is configured to perform a computer-implemented method for determining a consistency of registration of a position of the treatment body part to be treated by radiotherapy with the treatment beam arrangement of at least one position of the treatment beam issued by the treatment device, the treatment body part being a soft tissue part of an anatomical structure of a patient's body and the method comprising executing, on the at least one processor, steps of:
acquiring, by the at least one processor, first image data comprising predetermined first image information about a position of the treatment body part relative to a bony structure of the patient's body and about a first position of the bony structure relative to the treatment beam arrangement;
acquiring, by the at least one processor, second image data comprising second image information about a second position of the bony structure relative to the treatment beam arrangement;
determining, by the at least one processor and based on the second image data and the first image data by applying a fusion algorithm to the first image data and the second image data, bony structure position first transformation data comprising bony structure position first transformation information about a first transformation between the first position and the second position of the bony structure;
acquiring, by the at least one processor, third image data comprising third image information about a third position of the bony structure relative to the treatment beam arrangement and about the position of the treatment body part relative to the bony structure;
determining, by the at least one processor and based on the third image data and the first image data by applying a fusion algorithm to the third image data and the first image data, bony structure position second transformation data comprising bony structure position second transformation information about a second transformation between the first position and a third position of the bony structure relative to the treatment beam arrangement;

determining, by the at least one processor and based on the bony structure position first transformation data and the bony structure position second transformation data, transformation difference data comprising transformation difference information about a difference between the first and second transformations; and determining, by the at least one processor, based on the transformation difference data and the third image data and the first image data, whether there is an offset between the position of the treatment body part relative to the bony structure as it is described by the third image data and the position of the treatment body part relative to the bony structure as it is described by the first image data;

outputting movement control data to control the relative position of the treatment body part relative to the treatment beam if it is determined there is the offset between the position of the treatment body part relative to the bony structure as it is described by the third image data and the position of the treatment body part relative to the bony structure as it is described by the first image data.

2. The radiotherapy system of claim 1, wherein the first medical imaging device is a cone beam computed tomography-device, the first image is a cone-beam computed tomography image, the second image is an x-ray image, the second medical imaging device is a cone beam computed tomography-device, the third medical imaging device is an x-ray device, the first image data is computed tomography data, the second image data is x-ray data, the second image information is x-ray information, the predetermined first image information is predetermined computed tomography information, the third image data is cone beam computed tomography data, and the third image information is cone-beam computed tomography information.

3. The radiotherapy system of claim 1, wherein the system is constituted so that a position of the couch relative to the position of the treatment beam arrangement is controllable by the computer.

4. A method for controlling the radiotherapy system of claim 1, comprising issuing control signals from the computer to at least one of the couch and the treatment device for changing a relative position between the couch and the treatment beam arrangement.

5. A computer-implemented method for determining a consistency of registration of a position of a treatment body part to be treated by radiotherapy with a treatment beam arrangement of at least one position of a treatment beam issued by a treatment device, the treatment body part being a soft tissue part of an anatomical structure of a patient's body and the method comprising executing, on at least one processor of a computer, steps of:

acquiring, by the at least one processor, first image data comprising predetermined first image information about a position of the treatment body part relative to a bony structure of the patient's body and about a first position of the bony structure relative to the treatment beam arrangement;

acquiring, by the at least one processor, second image data comprising two-dimensional second image information about a second position of the bony structure relative to the treatment beam arrangement;

determining, by the at least one processor and based on the second image data and the first image data by applying a fusion algorithm to the first image data and the second image data, bony structure position first transformation data comprising bony structure position first transformation information about a first transformation between the first position and the second position of the bony structure;

acquiring, by the at least one processor, third image data comprising third image information about a third position of the bony structure relative to the treatment beam arrangement and about the position of the treatment body part relative to the bony structure;

determining, by the at least one processor and based on the third image data and the first image data by applying a fusion algorithm to the third image data and the first image data, bony structure position second transformation data comprising bony structure position second transformation information about a second transformation between the first position and a third position of the bony structure relative to the treatment beam arrangement;

determining, by the at least one processor and based on the bony structure position first transformation data and the bony structure position second transformation data, transformation difference data comprising transformation difference information about a difference between the first and second transformations; and determining, by the at least one processor, based on the transformation difference data and the third image data and the first image data, whether there is an offset between the position of the treatment body part relative to the bony structure as it is described by the third image data and the position of the treatment body part relative to the bony structure as it is described by the first image data;

outputting movement control data to control the relative position of the treatment body part relative to the treatment beam if the offset is determined indicating a difference in position of the treatment body part relative to the bony structure causing movement of the treatment body part relative to the treatment device.

6. The method according to claim 5, wherein the first image data is computed tomography data, the second image data is x-ray data, the second image information is x-ray information, the predetermined first image information is predetermined computed tomography information, the third image data is cone beam computed tomography data, and the third image information is cone-beam computed tomography information.

7. The method according to claim 5, further comprising:
checking, by the at least one processor application of the offset by determining whether an actual position of the bony structure relative to the treatment beam arrangement is equal to an expected offset.

8. The method according to claim 7, further comprising:
determining, by the at least one processor, if the step of checking results is that the actual position of the bony structure relative to the treatment beam arrangement is not equal to the expected offset, the movement control data for moving the patient by a difference between the second transformation and the offset.

9. The method according to claim 5, further comprising:
conducting, by the at least one processor and based on the transformation difference information, a calibration consistency check for the position of the bony structure relative to the position of the treatment beam.

10. The method according to claim 5, wherein the first image data, second image data and third image data are generated at each a different point in time.

11. The method according to claim 5, further comprising a step of generating, by the at least one processor, cone-beam computed tomography imaging control data comprising cone-beam computed tomography imaging control information for causing generation of the third image data after a period of time during which the treatment body part has been treated by a treatment beam.

12. A non-transitory computer-readable program storage medium storing a program which, when running on at least one processor of a computer or when loaded into a memory of a computer, causes the computer to perform a computer-implemented method for determining a consistency of registration of a position of a treatment body part to be treated by radiotherapy with a treatment beam arrangement of at least one position of a treatment beam issued by a treatment device, the treatment body part being a soft tissue part of an anatomical structure of a patient's body and the method comprising executing, on the at least one processor, steps of:

acquiring, by the at least one processor, first image data comprising predetermined first image information about a position of the treatment body part relative to a bony structure of the patient's body and about a first position of the bony structure relative to the treatment beam arrangement;

acquiring, by the at least one processor, second image data comprising second image information about a second position of the bony structure relative to the treatment beam arrangement;

determining, by the at least one processor and based on the second image data and the first image data by applying a fusion algorithm to the first image data and the second image data, bony structure position first transformation data comprising bony structure position first transformation information about a first transformation between the first position and the second position of the bony structure;

acquiring, by the at least one processor, third image data comprising third image information about a third position of the bony structure relative to the treatment beam arrangement and about the position of the treatment body part relative to the bony structure;

determining, by the at least one processor and based on the third image data and the first image data by applying a fusion algorithm to the third image data and the first image data, bony structure position second transformation data comprising bony structure position second transformation information about a second transformation between the first position and a third position of the bony structure relative to the treatment beam arrangement;

determining, by the at least one processor and based on the bony structure position first transformation data and the bony structure position second transformation data, transformation difference data comprising transformation difference information about a difference between the first and second transformations; and determining, by the at least one processor, based on the transformation difference data and the third image data and the first image data, whether there is an offset between the position of the treatment body part relative to the bony structure as it is described by the third image data and the position of the treatment body part relative to the bony structure as it is described by the first image data;

controlling the position of the treatment body part relative to the treatment beam if the offset is determined between the position of the treatment body part relative to the bony structure data and the position of the treatment body part relative to the bony structure causing movement of the treatment body part relative to the treatment device.

13. The program storage medium of claim 12, wherein the first image data is computed tomography data, the second image data is x-ray data, the second image information is x-ray information, the predetermined first image information is predetermined computed tomography information, the third image data is cone beam computed tomography data, and the third image information is cone-beam computed tomography information.

14. A computer comprising the program storage medium of claim 12.

* * * * *